United States Patent
Landis et al.

(10) Patent No.: US 8,738,307 B2
(45) Date of Patent: May 27, 2014

(54) METHOD FOR DETERMINING THE VISCOSITY OF A THIN FILM

(75) Inventors: Stefan Landis, Voiron (FR); Etienne Rognin, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 447 days.

(21) Appl. No.: 13/085,214

(22) Filed: Apr. 12, 2011

(65) Prior Publication Data

US 2012/0095705 A1    Apr. 19, 2012

(30) Foreign Application Priority Data

Apr. 13, 2010    (FR) ..................................... 10 01545

(51) Int. Cl.
  *G01N 11/00*         (2006.01)
(52) U.S. Cl.
  USPC ............................................. 702/50; 702/45
(58) Field of Classification Search
  USPC ........... 702/45, 50; 137/92; 73/54.01; 60/329
  See application file for complete search history.

(56) References Cited

U.S. PATENT DOCUMENTS

| | | | |
|---|---|---|---|
| 5,798,452 A | 8/1998 | Martin et al. | |
| 7,054,768 B2 * | 5/2006 | Anderson | ....................... 702/50 |
| 7,059,176 B2 * | 6/2006 | Sparks | ......................... 73/54.41 |
| 2009/0281242 A1 | 11/2009 | Landis | |

FOREIGN PATENT DOCUMENTS

| | | |
|---|---|---|
| EP | 0 801 734 B1 | 2/2005 |
| EP | 2 110 360 A2 | 10/2009 |
| FR | 2 936 360 A1 | 3/2010 |
| WO | 2010/034945 A1 | 4/2010 |

* cited by examiner

*Primary Examiner* — Elias Desta
(74) *Attorney, Agent, or Firm* — Baker & Hostetler LLP

(57) ABSTRACT

A method is provided for determining the viscosity of thin films which exhibit a viscous behavior at a measurement temperature, notably for polymer resins above their glass transition temperature. A thin layer of material is formed on a substrate, a known geometrical pattern is impressed in the thin layer by molding or etching, the thin layer being in the solid state at the end of the impression step. The initial topography of the impressed pattern is measured over the entire length of the pattern along a determined direction, the film is baked at the measurement temperature Tm for a determined creep time $t_{flu}$, and the resulting topography of the crept pattern is measured. Mathematical processing of the topography measurements is carried out in order to deduce a value of viscosity at the measurement temperature therefrom. The impressed pattern at the start is aperiodic.

14 Claims, 4 Drawing Sheets

5A

5B

5C

5D

5E

5F

5G

METHOD FOR DETERMINING THE VISCOSITY OF A THIN FILM

CROSS-REFERENCE TO RELATED APPLICATION

This application claims priority to foreign French patent application No. FR 1001545, filed on Apr. 13, 2010, the disclosure of which is incorporated by reference in its entirety.

FIELD OF THE INVENTION

The invention relates to a method for determining the viscosity of thin films which exhibit a viscous behavior at a measurement temperature, notably for polymer resins above their glass transition temperature, but also for inorganic materials above their melting temperature.

BACKGROUND

The conventional industrial techniques for measuring viscosity do not make it possible to carry out measurements on very thin films, for example films with a thickness of less than 10 micrometers.

For very thin films, various laboratory solutions have been proposed, notably measurement of the progressive leveling of a periodic pattern imposed in the layer of viscous film. Its principle is as follows: a periodic initial pattern is established in the film, for example a network of identical parallel linear ridges which are regularly spaced, each having a rectangular cross section; this pattern is for example impressed in the film at a temperature at which the film is viscous; the solidified impressed pattern is measured precisely, for example by means of an atomic force microscope; the spatial profile of the pattern is decomposed into a Fourier series; the film is heated to the temperature at which the viscosity is intended to be measured, for a determined time, which may be called the baking time; the pattern tends to become leveled more or less depending on the viscosity of the film at the measurement temperature; the film is cooled again in order to make it solid; the new geometrical profile of the periodic network is measured; this profile is decomposed into a Fourier series; calculation based on the fundamental coefficient of each of the two Fourier series makes it possible to determine a characteristic term, which is the ratio between the viscosity and the surface tension, if the average thickness of the film, the spatial period of the pattern and the time for which the pattern has been subjected to the measurement temperature are known; since the surface tension can be measured independently by other techniques, the viscosity can be calculated.

If the respective amplitudes of the fundamental coefficient of each of the two Fourier series are denoted as $a_0$ and $a_{flu}$, it is possible to write:

$$a_{flu}/a_0 = \exp(-t_{flu}/\tau)$$

where $t_{flu}$ is the baking time and $\tau$ is a time constant associated with the viscosity, which can be written $$\tau = 3\eta(1/\gamma h_0^3)(\lambda/2\pi)^4$$

where $\eta$ is the viscosity, $\gamma$ is the surface tension, $\lambda$ is the spatial period of the periodic pattern (the period which defines the fundamental frequency of the Fourier series) and $h_0$ is the average thickness of the layer.

One of the drawbacks of this method is the fact that measuring the viscosity by determining the ratio $a_{flu}/a_0$ makes sense only if this ratio is not too close to 1 and not too close to 0, which is equivalent to saying that if the periodic pattern has almost not moved during the baking time, or if the pattern is almost flattened after the baking, the measurement inaccuracies are too great to achieve a reliable determination of the viscosity.

It is therefore necessary to determine in advance a network geometry and a baking time and which will lead to a ratio $a_{flu}/a_0$ that is acceptable, for example not too far from 0.5, which means that it is necessary to know the likely value of the viscosity in advance with a good approximation. It is furthermore necessary for the selected baking time to be compatible with the possibilities of practical experimentation: a fairly long time in order to allow stabilization of the temperature of the film, but a fairly short time (less than one hour) in order to allow reasonable experimentation.

SUMMARY OF THE INVENTION

In order to assist measurement under good conditions, the invention provides a method for measuring the viscosity of a material in a thin layer at at least one measurement temperature Tm, comprising the formation of a thin layer of the material on a substrate, the impression by molding or etching of a known geometrical pattern in the thin layer, the thin layer being in the solid state at the end of the impression step, a measurement of the initial topography of the impressed pattern over the entire length of the pattern along a determined direction, heating to the measurement temperature Tm for a determined creep time $t_{flu}$, subsequent cooling to a solidification temperature of the layer, measurement of the topography resulting from the crept pattern, and mathematical processing of the topography measurements in order to deduce therefrom a value of viscosity at the measurement temperature, this method being characterized in that the impressed pattern of known geometry is an aperiodic pattern.

An aperiodic pattern is intended to mean a pattern which does not have a constant periodicity over the entire length of the measured topography in the measurement direction. In other words if the topography, that is to say the curve of height variations of the impressed pattern, is measured along an axis Ox, the initial impressed pattern has a vertical cross section along the axis Ox which, even if it is locally periodic, is not periodic over the entire length of the pattern along the axis Ox.

Preferably, the pattern is completely aperiodic, that is to say it does not include localized zones in which the pattern has a constant period, although an embodiment with locally periodic zones is possible.

The geometrical pattern impressed in the thin layer preferably consists of parallel grooves extending in a direction Oy perpendicular to a topography measurement direction Ox and having a rectangular cross section in a plane perpendicular to Oy and passing through Ox.

If the distance between an original sidewall of a groove having an abscissa x along Ox and an original sidewall of the next grove is denoted as $\lambda(x)$, this distance $\lambda(x)$ will be considered to be a variable "period" of the pattern, by analogy with the constant period of a periodic pattern, which is also a distance between two sidewalls of successive grooves. It is proposed according to the invention that the variation of the period $\lambda(x)$ preferably takes one of the following forms:

$$1/\lambda(x) = 1/\lambda_{max} + (1/\lambda_{min} - 1/\lambda_{max})x/L$$

or $$\lambda(x) = \lambda_{min}(\lambda_{max}/\lambda_{min})^{x/L}$$

or $$\lambda(x) = \lambda_{min} + (\lambda_{max} - X_{min})X/L$$

or $$\lambda(x) = \lambda_{min} + (\lambda_{max} - \lambda_{min})(X/L)^{1/4}$$

in which $\lambda_{min}$ and $\lambda_{max}$ are the minimum and maximum spatial periods (or edge-to-edge distances between grooves) in the impressed pattern, and L is the total length of the pattern.

The viscosity is preferably calculated in the following way:
  the coefficients of the discrete Fourier transform of the topography measured on the impressed pattern before creep are calculated,
  theoretical coefficients of a Fourier transform of a topography after creep are deduced therefrom according to a calculation formula involving a viscosity parameter, while varying the viscosity parameter in order to obtain a plurality of series of theoretical coefficients, each associated with a respective hypothetical viscosity,
  a series of experimental coefficients of the Fourier transform of the topography measured after creep is calculated,
  a search is carried out for optimal correlation between the series of experimental coefficients and the various series of theoretical coefficients, and a viscosity providing the best correlation is deduced therefrom.

The formula for calculating an $n^{th}$ order theoretical coefficient is preferably the following:

$$a_n^{tfu}(\eta) = a_n^0 \exp(-t_{flu}/\tau_n)$$

where $a_n^{tfu}(\eta)$ is the $n^{th}$ order theoretical Fourier coefficient of the topography after creep for a time $t_{flu}$, $a_n^0$ is the $n^{th}$ order coefficient of the topography measured on the impressed pattern after creep; and $\tau_n$ is a relaxation coefficient of the layer, associated with the viscosity $\eta$ by the relationship:

$$\tau_n = 3\eta(1/\gamma h_0^3)(L/2\pi n)^4$$

in which $\gamma$ is the surface tension of the thin layer; $h_0$ is its average thickness; L is the total length of the impressed pattern along the direction Ox.

In a variant of the mathematical processing, the position of a creep front along a pattern whose period varies continuously is observed while mathematically relating the position of this creep front at a known instant to the value of viscosity. Specifically, for a given creep time, the lower the viscosity is, the further the creep front will be away from the origin along the axis Ox (the origin being taken on the side with the shortest periods $\gamma$). The creep front may be defined as a fictitious boundary between a crept part and a not yet crept part of the geometrical pattern, for which boundary the peak-to-peak depth of the grooves has been reduced by a determined factor with respect to the depth of the original pattern (all the grooves having the same depth). At the time $t_{flu}$, or at any instant, it is possible to examine where this front is. The mathematical formula which makes it possible to deduce the viscosity therefrom will be returned to below.

BRIEF DESCRIPTION OF DRAWINGS

Other characteristics and advantages of the invention will become apparent on reading the following detailed description, which is given with reference to the appended drawings in which.

DETAILED DESCRIPTION

Figure 1:
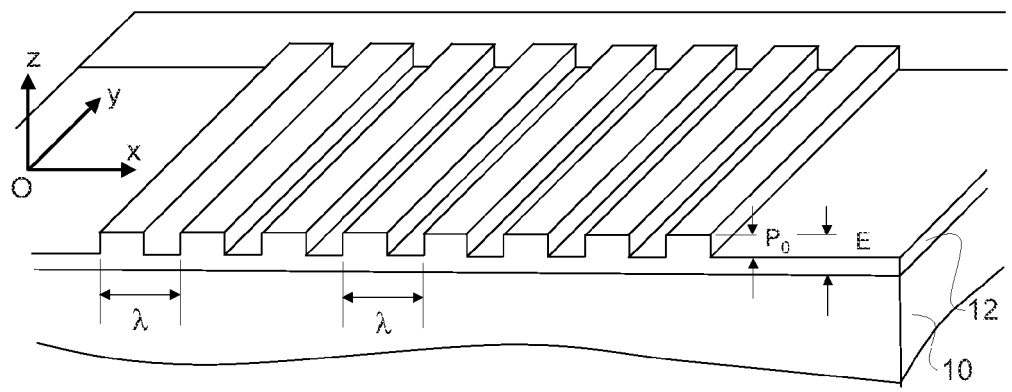
FIG. 1 represents in perspective a solid thin layer deposited on a substrate and shaped according to a periodic pattern.

In the prior art, in order to measure the viscosity of a material in a very thin layer, for example less than 10 micrometers, a layer 12 of this material has been deposited on a substrate 10 and has been shaped according to a periodic starting pattern as represented in FIG. 1; this pattern is a network of identical parallel grooves which extend along a direction Oy and are all spaced regularly in a direction Ox with a pitch $\lambda$ which may be referred to as the spatial "period" of the pattern; the grooves have a rectangular profile and their peak-to-peak depth is $P_0$. The depth $P_0$ is less than the total thickness E of the layer, so that the bottoms of the grooves are not in contact with the material of the substrate. The width of the plateaus which separate the grooves may be equal to the width of the grooves.

Figure 2:
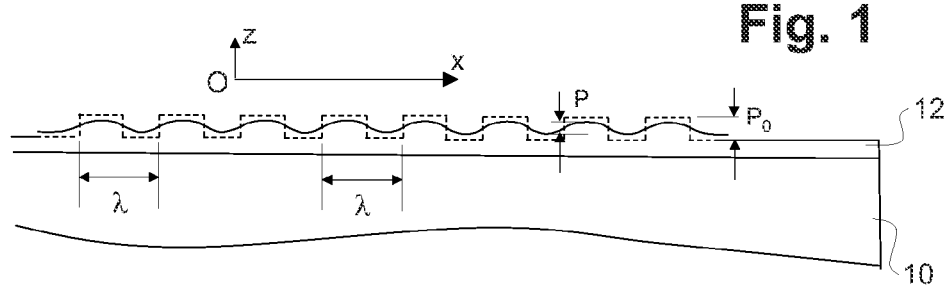
FIG. 2 represents this thin layer in vertical section after creep at a temperature above the glass transition.

The layer is in the solid state at the start, that is to say at the start it is at a temperature lower than the glass transition temperature. When the thin layer is heated to a measurement temperature Tm above the glass transition temperature for a creep time $t_{flu}$, the layer becomes leveled progressively and in a regular way, as represented in FIG. 2 (the profile of the curve before creep is represented by dashes). Starting from rectangular grooves with a depth $P_0$, grooves with a rounded profile of peak-to-peak depth P are obtained. The ratio between $P_0$ and P is directly associated with the viscosity, or more precisely with the ratio between the viscosity and the surface tension of the material, since a material with very high viscosity will deform less than a material with lower viscosity for the same creep time.

In order to calculate the ratio between $P_0$ and P, it is best to measure the curve of height (measured along a vertical axis Oz by means of an atomic force microscope) as a function of the horizontal distance (along Ox) over the entire length of the pattern. By taking a Fourier transform of this measurement, an amplitude coefficient is immediately found for the fundamental spatial frequency, which is determined by the period $\lambda$ of the network. The transform is taken for the curve of the height of the layer before creep and for the curve of the height of the layer after creep. The ratio between the first coefficients of the transform makes it possible to calculate the viscosity.

In summary, in FIGS. 1 and 2 a starting pattern is used which is a simple periodic network, the Fourier transform of which essentially comprises a fundamental frequency and its harmonics (the harmonics are associated with the fact that the starting pattern is rectangular and not sinusoidal), only the fundamental frequency being used for determining the viscosity.

According to the invention an aperiodic network is used, the spectrum of which cannot be characterized by a fundamental frequency with a large amplitude and its harmonics with smaller amplitudes.

Two types of aperiodic networks are principally envisaged here:
a completely aperiodic network, having no local zones with a constant spatial period; such a network may consist of a set of parallel grooves having widths and spacings which are continuously variable from one line to the next;
a partially aperiodic network having successive zones with a constant spatial period, the period varying from one zone to the next; such a network may consist of a set of parallel grooves organized in juxtaposed successive groups, the grooves of one group having a constant width and a constant spacing which are different to the width and spacing of the other groups.

Figure 3:
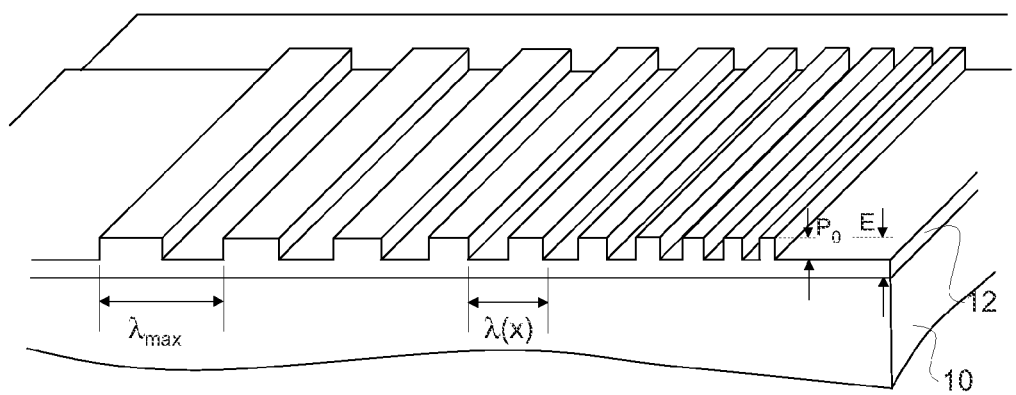
FIG. 3 represents a solid thin layer shaped according to an aperiodic pattern.

FIG. 3 represents in perspective an example of a network of parallel grooves with a spatial "period" which is continuously variable along the axis Ox (the axis perpendicular to the lengthwise direction of the grooves). It is a completely aperiodic network; consequently, the word "period" is used here by analogy with the periodic network of the prior art; the spatial period is the width, in the direction Ox, of a groove and a plateau separating it from the next groove, that is to say the distance which separates the start of an assembly comprising a groove and a plateau adjacent to the groove from the start of a subsequent assembly consisting of a groove and a plateau. The spatial period varies according to a function $\lambda(x)$ that can take various forms, which will be returned to below. The period varies between a value $\lambda_{min}$ and a value $\lambda_{max}$. The range of viscosities which can be measured is commensurately greater when the ratio $\lambda_{max}/\lambda_{min}$ is greater.

As in FIG. 1, the depth $P_0$ of the grooves of the starting pattern impressed on the solidified layer is less than the total thickness E of the layer.

Figure 4:
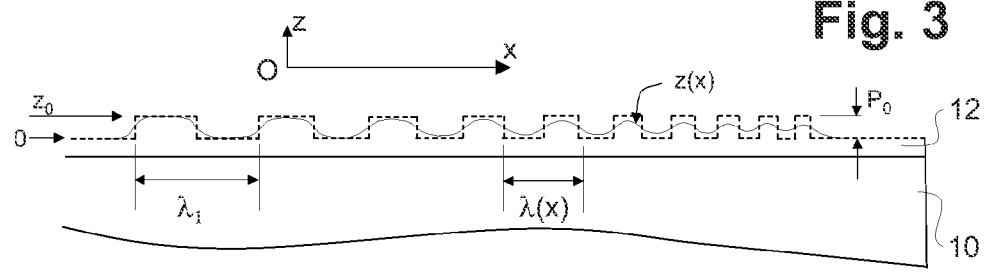
FIG. 4 represents the layer of FIG. 3 after creep at a temperature above the glass transition.

FIG. 4 represents the result of the creep of the pattern of FIG. 3 for a time $t_{flu}$ at a measurement temperature Tm higher than the glass transition temperature. The profile of the network will be leveled to a greater or lesser extent depending on the temperature and the duration of the creep, but it can be seen that the leveling is not uniform and does not lead to a groove depth which is constant over the entire network, as was the case in FIG. 2. Specifically, where the lines are spaced apart the most, the depth of the bottoms remains almost equal to the starting depth $P_0$, but where they are spaced apart less the depth becomes very much less than $P_0$.

The depth of the grooves will therefore not be addressed, as was done with the periodic pattern of FIG. 1; instead, the complete profile of the height variations z(x) of the layer as a function of the position on the axis Ox will be addressed.

The base of the grooves of the starting solid layer may be taken as a height reference 0, the height of the layer at the top of the plateaus which separate the grooves in the starting pattern being $z_0 = P_0$, or alternatively the bottom of the thin layer may be taken as a height reference 0, the height of the layer in the grooves being $E - P_0$ and the height of the plateaus being E.

Depending on the viscosity of the layer (for a given creep time $t_{flu}$), there will be different creep profiles, and it is seen that even for high viscosities there may be a significant height variation (neither too close to the starting profile nor too leveled) where the lines are particularly close together, while for low viscosities the height variation will be more significant where the lines are less close together, the layer being almost leveled where the lines are closest together.

This makes it possible to analyze samples even if there is little information a priori about the approximate value of the viscosity to be found.

The analysis may be carried out in several ways, but in all cases it will be noted that the same sample can be used to carry out a plurality of successive analyses:
for example, a plurality of analyses at the same measurement temperature, in order first to observe the creep over a first time and obtain a first viscosity determination, then recommence the creep starting from the point at which it had arrived in order to carry out another viscosity determination,
or alternatively a plurality of analyses at different successive measurement temperatures in order to measure the viscosity at these temperatures, starting with the lowest temperatures.

The way in which the profiles, before and after creep, of the heights z(x) of the layer along the axis Ox are processed in order to obtain a viscosity value, despite the fact that the height profile is aperiodic both before creep and after creep, will be described below.

Figure 5:
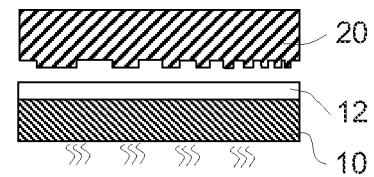
FIG. 5 schematically represents the principal steps of the method according to the invention.
Figure 5:
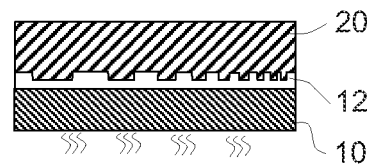
Figure 5:
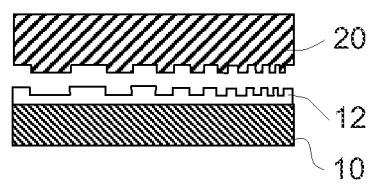
Figure 5:
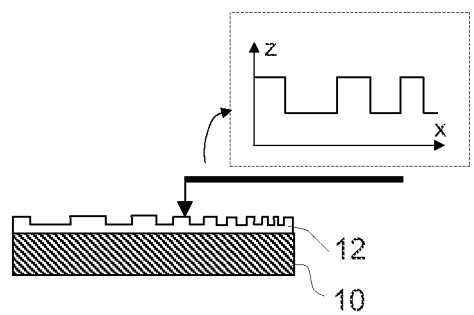
Figure 5:
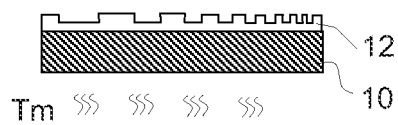
Figure 5:
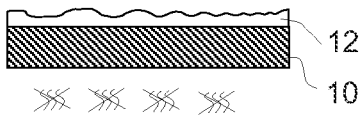
Figure 5:
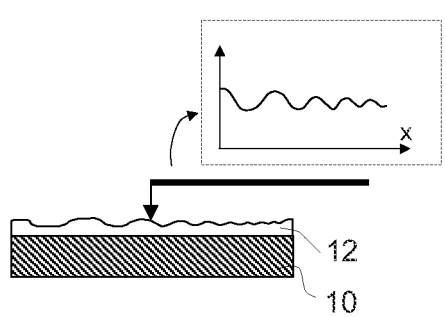

FIG. 5 represents the principal steps of the method according to the invention.

The first step is to deposit the layer 12 to be analyzed on a substrate 10. In the case of an organic polymer layer, the layer may be deposited for example by spin-coating or by sputtering. If the layer is mixed with a solvent in order to facilitate deposition, the layer will then be baked in order to remove the solvent, then it will be cooled to room temperature in order to form a solid film of constant thickness on the substrate.

The average thickness $h_0$ of the layer is measured, for example by ellipsometric techniques. The measurement may be carried out on the layer in the solidified state or in the viscous state.

At 5A: the substrate and the layer are heated before impressing on the latter's surface an aperiodic starting pattern of known geometry, which may be the one in FIG. 3.

At 5B: the pattern is hot-impressed in the layer by means of a mold 20 etched according to the desired pattern. The heating is carried out to a liquefaction temperature which is sufficient for the layer to adopt the shape of the mold exactly: this is a temperature above the glass transition temperature or even above the melting temperature for an inorganic material, but of course below its breakdown or boiling temperature. The molding temperature is independent of the measurement temperature at which the viscosity is intended to be measured. The depth of the imprints of the mold is less than the thickness of the layer to be impressed ($P_0 < E$) according to FIG. 3.

At 5C: the mold is cooled to a solidification temperature of the thin layer (which may be room temperature), followed by mold release in order to obtain the starting pattern on the solidified layer 12.

The impression of the pattern in the layer could also be obtained, in particular for inorganic materials, by a photolithography method with a mask defining the pattern, or alternatively by etching by means of an electron beam controlled as a function of the pattern to be produced.

The mold itself will be produced by lithography techniques with or without a mask, with a resolution which is as high as possible.

At 5D: the height curve z(x) of the sample prepared in this way is plotted. This curve represents the height variations of the surface of the thin layer along the axis Ox perpendicular to the lines of the pattern impressed in the layer. It will be assumed for simplicity that the pattern comprises parallel lines with a constant cross section along Oy, that is to say the pattern can be considered to be two-dimensional, although the method could be adapted to a three-dimensional pattern in which the height varies not only along Ox but also along Oy, which is perpendicular to Ox and Oz. A crossed network of rows and columns may for example be envisaged, the network of rows being completely aperiodic or partially aperiodic and the network of columns being periodic or aperiodic.

The heights along Ox are preferably measured by an atomic force microscope or by a scanning tunneling microscope (STM microscope); these microscopes make it possible to carry out topographic height measurements with precisions of the order of one nanometer.

At 5E: the thin layer is heated to the measurement temperature Tm for which the viscosity is intended to be known, for a creep time $t_{flu}$. The creep time is selected very approximately as a function of what is known of the viscosity of the thin layer at the temperature Tm, but the aperiodic network permits measurement in a very wide range of viscosities, and therefore in a wide range of creep times.

At 5F: the heating is stopped and the thin layer is cooled rapidly so that it solidifies in a partially leveled (but of course not completely leveled) state.

At 5G: a height curve z(x) of the sample is again plotted along the same line parallel to Ox as during the first measurement and according to the same height reference and the same height scale. The same measurement tool, atomic force microscope or STM microscope, is used.

As indicated above, steps 5E, 5F, 5G may be repeated several times, as follows:
 with the same temperature and the same duration, in order to continue the creep,
 or with the same temperature and different durations,
 or with a different temperature and the same duration or different directions.

Only a single group of steps 5E, 5F, 5G will be considered below.

A comparison of the curves before and after creep makes it possible to infer information about the viscosity.

This comparison is preferably carried out by taking a discrete Fourier transform of the curves of height before and after creep.

The height of the layer (that is to say of the upper surface of the layer) is described by a strictly positive function z(x). The length of the full pattern along the axis Ox is L. This length is selected as a function of the capabilities of the measurement means; for example, L=40 or 50 micrometers for a measurement by an atomic force microscope, or several hundreds of micrometers for a measurement by a profilometer or by an optical microscope.

Contrary to what has been represented in the various figures in order to make them easier to read, it will be assumed that the height variations of the layer are small compared with the average thickness of the layer.

The Fourier transforms of the height curve are taken under the same conditions for the curve before creep and the curve after creep. They each result in N coefficients (the same number N for both curves). The $n^{th}$ order coefficient of the Fourier transform of the starting curve before creep is denoted as $a_n^0$, and the $n^{th}$ order coefficient of the Fourier transform at the instant $t_{flu}$ (end of the creep) is denoted as $a_n^{tflu}$.

By making simplifying assumptions, it can be shown that the theoretical value of this $n^{th}$ order coefficient depends on the viscosity $\eta$; this theoretical value is denoted as $a_n^{tflu}(\eta)$, and it is such that:

$$a_n^{tflu}(\eta)/a_n^0 = \exp(-t_{flu}/\tau_n)$$

where $\tau_n$ is a characteristic relaxation time specific to the $n^{th}$ order coefficient of the Fourier transform. Moreover, it can be shown that this relaxation time can be approximated by:

$$\tau_n = 3\eta(1/\gamma h_0^3)(L/2\pi n)^4$$

where $\eta$ is the viscosity, $\gamma$ is the surface tension of the layer at the temperature in question (this is assumed to be known if the viscosity is intended to be found, but it does not need to be known if only the ratio $\eta/\gamma$ is intended to be found), $h_0$ is the average thickness of the layer, L is the total length of the pattern.

Since the viscosity is not known, theoretical calculations will be carried out with a series of different viscosity values and a correlation search will be performed in order to find what is the optimal viscosity $\eta_{opt}$ which gives a series of theoretical coefficients $a_n^{tflu}(\eta_{opt})$ closest to the series of values $a_n^{tflu}$ obtained by Fourier transform of the height curve actually measured after creep.

The value of the viscosity (or the ratio $\eta/\gamma$) will therefore be varied first, while trying to find a series of theoretical coefficients $a_n^{tflu}(\eta)$ for each viscosity value, on the basis of the Fourier transform of the initial height curve. The Fourier transform of the experimentally measured curve will be taken in parallel in order to obtain a series of coefficients $a_n^{tflu}$. The optimal viscosity value which makes the two series coincide as well as possible will then be looked for.

The ratio $\lambda_{max}/\lambda_{min}$ between these maximum and minimum values determines the ratio between the maximum and minimum viscosities which can be measured with the pattern for a given creep time. $\lambda_{min}$ is determined by the resolution capabilities of the technology used to impress the pattern in the layer. $\lambda_{max}$ must be small compared with L, preferably at least 5 to 10 times smaller. The resolution criterion can be expressed in the following way: it is necessary for the product of $\lambda_{min}$ times the rate of increase $d\lambda/dx$ of the period per unit distance along the axis Ox to be greater than or equal to two times the resolution (which may be denoted as $\delta r$) permitted by the technology:

$$\lambda_{min} \cdot d\lambda/dx >= 2\delta r$$

(the rate of increase $d\lambda/dx$ considered here is the rate at the position where the period is $\lambda_{min}$).

A ratio $\lambda_{max}/\lambda_{min}$ of maximum and minimum periods will preferably be selected as a function of a viscosity range to be measured (with a constant creep temperature and constant creep time), then a value $\lambda_{min}$ satisfying the resolution criterion, and it will be checked that the variation profile selected for changing from $\lambda_{min}$ to $\lambda_{max}$ leads to a sufficiently small value $\lambda_{max}$ compared with the total length L of the pattern. If this is not the case, the ratio $\lambda_{max}/\lambda_{min}$ will be reduced and the procedure will be started again.

The following examples show several types of patterns, that is to say variation profiles of the period along the axis Ox, which may be used advantageously according to the invention.

1. Pattern with Uniform Spectral Density

Uniformity of the spectral density makes it possible to utilize both the small periods of the pattern and the large ones.

Such uniformity may be obtained by varying the period $\lambda(x)$ for example according to the formula:

$$1/\lambda(x) = 1/\lambda_{max} + (1/\lambda_{min} - 1/\lambda_{max})x/L$$

2. Pattern for a Creep Front with Constant Speed

A pattern will be considered whose period varies continuously, for example by decreasing progressively from left to right. During the baking at the temperature Tm, the creep will be manifested initially on the right, where the period is the smallest, then progressively more and more toward the left. A method for measuring the viscosity may consist in observing the change in this progressive extension of the crept zone, from left to right, using a microscope. For example, a creep front may be defined which is a position varying as a function of time along the axis Ox and which schematically represents the boundary between an already crept zone and a not yet crept zone, the displacement of this creep front as a function of time being observed.

It can be shown that if the period variation as a function of x is small (for example $d\lambda/dx$ is less than or equal to $10^{-3}$), then the height profile $z(x)$ is modulated with an amplitude envelope proportional to $\exp[-t/\tau(x)]$ where $\tau(x)$ is the time constant corresponding to the period $\lambda(x)$: $\tau(x)=3\eta(1/\gamma h_0^3)[\lambda(x)/2\pi]^4$. This is equivalent to saying that the local relaxation constant at x is the same as if the pattern was periodic and had a spatial period $\lambda(x)$.

In this case, it is possible to arbitrarily define a creep front and observe its displacement. The creep front is the abscissa along Ox for which the relative amplitude is decreased by a factor of $e^{-\alpha}$ with respect to the amplitude of the ridges of the initial pattern. The coefficient $\alpha$ may be selected arbitrarily, and will depend on the measurement device used to carry out the observation. For example, if $\alpha=3$, the position of the creep front will be considered to be that for which the pattern has decreased by 5%, although another value could be selected, for example $\alpha=0.69$, in order to define the creep front by the position where the amplitude has decreased by 50%. The abscissa of the creep front is $x_a(t)$ at an instant t.

Figure 6:
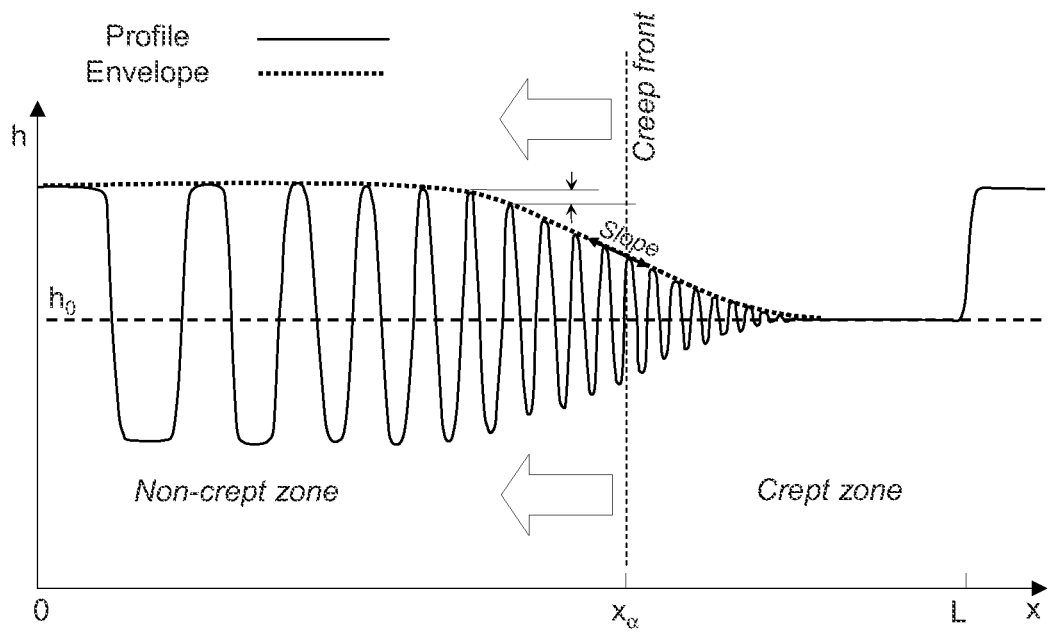
FIG. 6 represents a curve of the height of a crept profile, showing the envelope of the curve and a creep front between a crept zone and a not yet crept zone.

FIG. 6 illustrates an example of a profile of a pattern at an instant t at the start of heating to the measurement temperature Tm. The creep front has been placed at a position corresponding to a coefficient $\alpha=0.69$.

A video camera may be used in order to measure the displacement rate of the creep front as a function of time.

It can be shown that by selecting a pattern whose period varies according to the form:

$$\lambda(x)=\lambda_{min}+(\lambda_{max}-\lambda_{min})(x/L)^{1/4};$$

the interesting result is obtained that the speed of the creep front along the pattern is constant and that the speed is equal to $L/\alpha \cdot \tau(L)$ where $\tau(L)$ is the relaxation constant at the abscissa L, that is to say at the position where the period of the pattern is the smallest ($\lambda_{min}$)

$$\tau(L)=3\eta(1/\gamma h_0^3)[\lambda_{min}/2\pi]^4$$

Based on the observed speed, it is therefore possible to obtain the viscosity.

This form of period variation may also be adopted when trying to find a viscosity value by Fourier transform calculations and an optimization by correlation between theoretical values of coefficients and values resulting from a height measurement (cf. above).

3. Pattern for a Maximum Slope of the Creep Front

In order to have a high contrast between the crept zone (on the right in FIG. 6) and the not yet crept zone (on the left), a large slope of the envelope is required at the position of the creep front, this applying at all times during the creep.

It can be shown that this is achieved by using an aperiodic pattern whose local period $\lambda(x)$ varies exponentially from to $\lambda_{min}$ to $\lambda_{max}$:

$$\lambda(x)=\lambda_{min}(\lambda_{max}/\lambda_{min})^{x/L}$$

4. Pattern for a Constant Height Difference at the Creep Front

The peak-to-peak height difference between two consecutive ridges is an interesting parameter, which approximately corresponds to the slope, in any event for the smallest periods of the pattern. If it is desirable for the peak-to-peak height difference to be constant as a function of time, it can be shown that it is necessary to select a linear variation of the period $\lambda(x)$:

$$\lambda(x)=\lambda_{min}+(\lambda_{max}-\lambda_{min})x/L$$

One advantage of the invention is that the range of viscosities which can be measured depends not only on the ratio between the minimum and maximum creep times ($t_{max}$ and $t_{min}$) that the experimentation makes it possible to use (in practice, $t_{min}$ is of the order of one minute and $t_{max}$ is of the order of one hour), but also on the ratio between the periods $\lambda_{max}$ and $\lambda_{min}$ of the pattern, and more precisely on this ratio raised to the $4^{th}$ power:

$$\eta_{max}/\eta_{max}=(t_{max}/t_{min}) \cdot (\lambda_{max}/\lambda_{min})^4$$

If $\lambda_{max}/\lambda_{min}$ is equal to 2, the range of viscosities which can be measured is multiplied by 16; if $\lambda_{max}/\lambda_{min}$ is equal to 10, the range of viscosities which can be measured is multiplied by 10 000.

Furthermore, a plurality of different geometrical patterns having adjacent or overlapping ranges of periods may be placed on the same substrate. Adjacent ranges for two patterns A and B means that the maximum period $\lambda^A_{max}$ of a pattern A is equal to the minimum period $\lambda^B_{min}$ of a pattern B. Overlapping ranges means the fact that the maximum period $\lambda^A_{max}$ of a pattern A is greater than the minimum period $\lambda^B_{min}$ of a pattern B but less than the maximum period $\lambda^B_{max}$ of the pattern B.

Overlap is useful in order to confirm a measurement. Too great an overlap, however, would be inexpedient. One interesting solution may be, in the event that there are three patterns A, B, C with overlapping ranges of periods $\lambda_{min}$, $\lambda_{max}$, that the overlap of period ranges is complete (overlap of ranges everywhere) but unique or non-redundant, that is to say there is no period value which belongs to all three patterns.

The latter result is achieved with patterns having a range of periods ($\lambda_{min}$, $\lambda_{max}$) such that $\lambda_{max}/\lambda_{min}$=R is constant for all the patterns and by providing that the minimum period $\lambda_{min}$ of a pattern B is equal to $R^{1/2}$ times the minimum period of a pattern A.

In the description above, it was assumed that the period variation $\lambda(x)$ is known, although in a particular embodiment it is assumed that the aperiodic pattern consists of a succession of adjacent periodic subpatterns having different periods from one another distributed between two spatial periods, one minimum and one maximum, $\lambda_{min}$ and $\lambda_{max}$. The principles explained above for calculating the viscosity on the basis of the discrete Fourier transforms remain applicable. The variation of the period between $\lambda_{min}$ and $\lambda_{max}$ has become a staircase function.

By way of illustration, the way in which the viscosity of a 30 k (molar mass 30 kg/mole) polystyrene thin layer can be measured at 120° C. will be described.

The surface tension of this material at 120° C. is known; it is $\gamma=32$ mN/m.

An atomic force microscope will be used in order to determine the profiles along Ox of the pattern impressed in the thin layer. The maximum length of a measurement for the apparatus used is 40 micrometers.

The pattern will be impressed by a mold having a resolution of 5 nanometers.

In this case, a geometrical pattern could preferably be selected whose period $\lambda(x)$ varies as a function of the abscissa x according to a function which tends to make the spectral density uniform, such as the function (mentioned above) defined by the equation $1/\lambda(x)=1/\lambda_{max}+(1/\lambda_{min}-1/\lambda_{max})x/L$. Other likewise satisfactory patterns may also be selected, and in this example the one which is defined by the equation $\lambda(x)=\lambda_{min}(\lambda_{max}/\lambda_{min})^{x/L}$ (mentioned above) is selected.

A ratio $\lambda_{max}/\lambda_{min}$ equal to 10 is furthermore selected arbitrarily.

The resolution criterion explained above means that the product of $\lambda_{min}$ times the derivative of $\lambda(x)$ with respect to x (for $\lambda=\lambda_{min}$) is more than two times the resolution, and therefore greater than or equal to 10 nanometers in this example. Now, the derivative of the function $\lambda(x)$ for $\lambda=\lambda_{min}$, that is to say for x=0 in this case, is equal to $\lambda_{min}[\ln(\lambda_{max}/\lambda_{min})]/L$ here.

It is concluded from this that it is necessary to have $\lambda^2_{min}[\ln(\lambda_{max}/\lambda_{min})]/L$ greater than or equal to 10 nanometers (two times the resolution), which gives $\lambda_{min}$ at least equal to 417 nanometers.

A $\lambda_{max}$ of 4.17 micrometers is therefore obtained, which is still small compared with the measurement length L=40 micrometers.

If this was not the case, the ratio $\lambda_{max}/\lambda_{min}$ would be reduced and the calculation would be redone.

Figure 7:
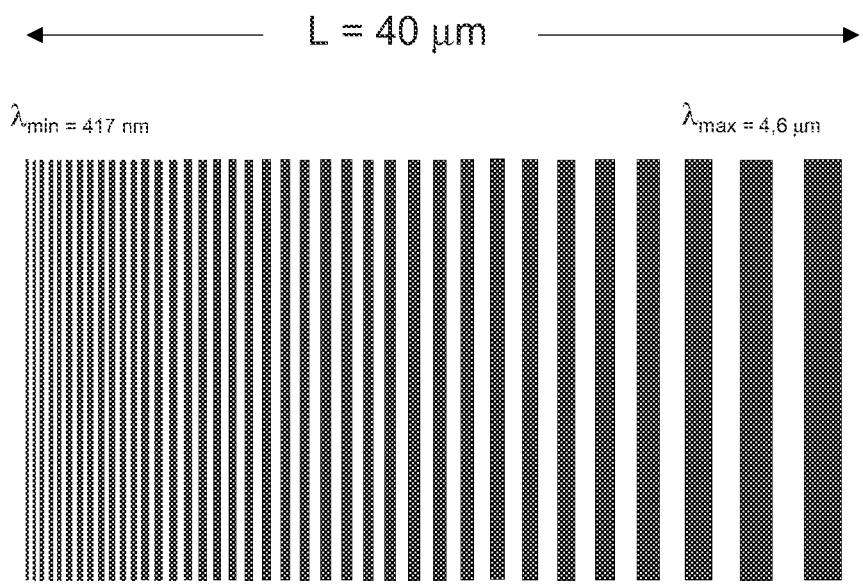
FIG. 7 represents a geometrical pattern used in an experiment.

FIG. 7 represents a mold configuration for impressing the corresponding pattern on a sample of a substrate covered with a layer of polystyrene. The mold may be produced by photolithography. The depth of the impressed grooves is 45 nanometers.

The polystyrene is preferably deposited on a silicon substrate by spin-coating. To this end, it may be diluted to 2% in toluene. The rotation speed of the substrate may be 1000 revolutions per minute. Baking at 150° C. then makes it possible to evaporate the toluene. The film obtained is homogeneous and flat. Its total thickness measured by ellipsometry is 147 nanometers in the experiment carried out. The average thickness of the film is 125 nanometers.

Figure 8:
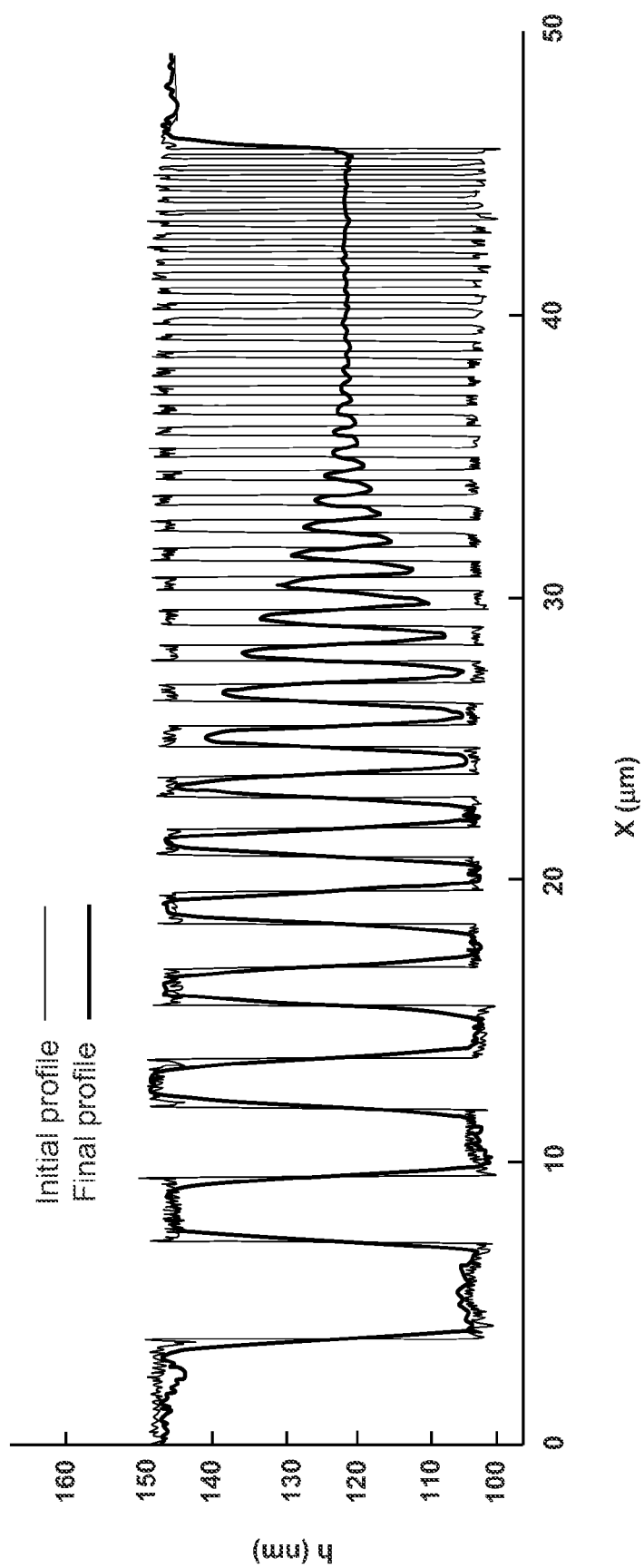
FIG. 8 represents the height curves plotted in this experiment, before and after creep.

The geometrical pattern of FIG. 7 is impressed using the mold, heated to 170° C., with a contact pressure of 13 bar for 5 minutes. The mold is cooled to room temperature and the sample is released from the mold. A first measurement with an atomic force microscope gives an initial profile which is represented in FIG. 8 (thinner line). If the variation in the period as a function of x was in staircase form, there would be a different starting curve.

The film is heated to a measurement temperature Tm which in this experiment is 120° C., for a creep time $t_{flu}$ which in this example is 5 minutes. The film is then cooled abruptly (1 second) to room temperature in order to fix the pattern obtained at the end of the creep time.

The crept profile is measured with an atomic force microscope, leading to the height curve in FIG. 8 (thicker line).

The mathematical processing of the curves of FIG. 8 comprises first a discrete Fourier transform of these curves, giving coefficients for each profile. The $n^{th}$ order coefficient is $a_n^0$ for the starting curve and $a_n^{tflu}$ for the curve after creep.

For each viscosity value $\eta$ taken from a series of possible values, a relaxation time $\tau_n=3\eta(1/\gamma h_0^3)(L/2\pi n)^4$ is calculated.

From this relaxation time, which is dependent on n and $\eta$, theoretical Fourier coefficients are deduced by the formula $$a_n^{tflu}(\eta)=a_n^0\exp(-t_{flu}/\tau_n)$$

For each hypothetical value of viscosity, a series of expected Fourier coefficients is obtained.

This series is compared with the series of coefficients $a_n^{tflu}$ calculated from the height curve measured experimentally after creep.

The optimal viscosity $\eta_{opt}$ which makes the series resulting from the viscosity hypothesis correspond best to the series of values calculated from the experimental measurement is determined. This optimal value $\eta_{opt}$ is an estimate of the actual viscosity of the thin layer.

In the experiment carried out above, an optimal $\eta_{opt}=6.4\times 10^6$ Pa·s was found.

It will be noted that not only the viscosity but also the modulus of elasticity of the material in a thin layer can be measured by this method.

For example, a polymer melted at a temperature close to its glass transition temperature ($T_g$) has a behavior termed viscoelastic (for example, polystyrene at a temperature $T_g$ of +20° C.).

For low-frequency mechanical stresses (that is to say with long times, for example a few minutes), the material has a viscous fluid behavior: it flows. For rapid stresses on the other hand (short times, a few seconds in our example), the material has an elastic behavior: it deforms without flowing and gives back the deformation energy like a spring. This dichotomy of the behaviors between short times and long times is measured by a characteristic time, denoted as $\tau_{relax}$, which is the characteristic relaxation time of the elastic stresses. This time is involved in modeling the creep of a nanostructured thin layer, via the characteristic decay time of the mode n, expressed in the purely viscous case by the formula used above: $\tau_n=3\eta(1/\gamma h_0^3)(L/2\pi n)^4$ with $\eta$ the viscosity, $\gamma$ the surface tension $h_0$ the average thickness of the film and L the length of the profile measured. In modeling of the simpler case of viscoelasticity, we will have a slightly different formula which involves the characteristic relaxation time of the elastic stresses $\tau_{relax}$:

$$\tau_n=\tau_{relax}+3\eta(1/\gamma h_0^3)(L/2\pi n)^4.$$

As before, a search for optimal correlation may be carried out by starting with hypotheses of values of the viscosity $\eta$ and the time $\tau_{relax}$, so as to obtain an optimal pair of values $\eta_{opt}, \tau_{relax-opt}$.

The modulus of elasticity E of the material is then calculated by the formula: $E=\eta_{opt}/\tau_{relax-opt}$.

The method therefore uses in summary the same calculation steps as previously, before calculating the modulus of elasticity; these steps are: calculation of a theoretical $n^{th}$ order coefficient of the Fourier transform for a hypothetical viscosity $\eta$:

$$a_n^{tflu}(\eta)=a_n^0\exp(-t_{flu}/\tau_n)$$

where $a_n^{tflu}(\eta)$ is the theoretical $n^{th}$ order Fourier coefficient of the topography after creep for a time $t_{flu}$, $a_n^0$ is the $n^{th}$ order coefficient of the topography measured on the impressed pattern after creep; and $\tau_n$ is a relaxation coefficient of the layer, associated with the viscosity $\eta$ by the relationship:

$$\tau_n=\tau_{relax}+3\eta(1/\gamma h_0^3)(L/2\pi n)^4$$

in which $\gamma$ is the surface tension of the thin layer; $h_0$ is its average thickness and L is the total length of the impressed pattern, and $\tau_{relax}$ is a characteristic relaxation time of elastic stresses, the calculation being carried out for different hypothetical viscosities $\eta$ and different characteristic times $\tau_{relax}$, and an optimal pairing of a viscosity $\eta_{opt}$ and a characteristic time $\tau_{relax-opt}$ being selected in the optimal correlation search.

The invention claimed is:

1. A method for measuring the viscosity of a material in a thin layer at least one measurement temperature Tm, comprising:
   the formation of a thin layer of said material on a substrate,
   the impression by molding or etching of a known geometrical pattern in the thin layer, the thin layer being in the solid state at the end of the impression step, a measurement of the initial topography of the impressed pattern over the entire length of the pattern along a determined direction, heating to said measurement temperature Tm for a determined creep time $t_{flu}$, subsequent cooling to a solidification temperature of the thin layer, measurement of the topography resulting from the crept pattern, and mathematical processing of the topography measurements carried out by a computer processor in order to deduce therefrom a value of viscosity at the measurement temperature, outputting of a value of viscosity at the measurement temperature, wherein the impressed pattern of known geometry is a generally aperiodic pattern.

2. The method as claimed in claim 1, wherein the impressed pattern does not include locally periodic zones.

3. The method as claimed in claim 1, wherein the pattern is includes locally periodic subpatterns having different periods to one another.

4. The method as claimed in claim 1, wherein the geometrical pattern impressed in the thin layer comprises parallel grooves extending in a direction Oy perpendicular to a topography measurement direction Ox and having a rectangular cross section in a plane perpendicular to Oy and passing through Ox, the parallel grooves having a spatial period k(x) which is variable along the axis Ox, the spatial period being the width, in the direction Ox, of one groove and a plateau separating said one groove from a following groove.

5. The method as claimed in claim 4, wherein the period $\lambda(x)$ varies according to the following function:

$$1/\lambda(x)=1/\lambda_{max}+(1/\lambda_{min}-1/\lambda_{max})x/L,$$

in which $\lambda_{min}$ and $\lambda_{max}$ are a minimum and maximum spatial periods in the impressed pattern, and L is a total length of the pattern.

6. The method as claimed in claim 4, wherein the period $\lambda(x)$ conforms to the function:

$$\lambda(x)=\lambda_{min}(\lambda_{max}/\lambda_{min})^{x/L},$$

in which $\lambda_{min}$ and $\lambda_{max}$ are a minimum and maximum spatial periods in the impressed pattern, and L is a total length of the pattern.

7. The method as claimed in claim 4, wherein the period $\lambda(x)$ conforms to the function:

$$\lambda(x)=\lambda_{min}+(\lambda_{max}-\lambda_{min})x/L,$$

in which $\lambda_{min}$ and $\lambda_{max}$ are a minimum and maximum spatial periods in the impressed pattern, and L is a total length of the pattern.

8. The method as claimed in claim 4, wherein the variation of the period $\lambda(x)$ conforms to the function:

$$\lambda(x)=\lambda_{min}+(\lambda_{max}-\lambda_{min})(x/L)^{1/4},$$

in which $\lambda_{min}$ and $\lambda_{max}$ are a minimum and maximum spatial periods in the impressed pattern, and L is a total length of the pattern.

9. The method as claimed in claim 1, wherein the viscosity is calculated in the following way:

coefficients of the discrete Fourier transform of the topography measured on the impressed pattern before creep are calculated, theoretical coefficients of a Fourier transform of a topography after creep are deduced therefrom according to a calculation formula involving a viscosity parameter, while varying the viscosity parameter in order to obtain a plurality of series of theoretical coefficients, each associated with a respective hypothetical viscosity, a series of experimental coefficients of the Fourier transform of the topography measured after creep is calculated, and a search is carried out for optimal correlation between the series of experimental coefficients and the various series of theoretical coefficients, and a viscosity providing the best correlation is deduced therefrom.

10. The method as claimed in claim 9, wherein the formula for calculating an $n^{th}$ order theoretical coefficient of the Fourier transform for a hypothetical viscosity $\eta$ is:

$$a_n^{tflu}(\eta)=a_n^0 \exp(-t_{flu}/\tau_n),$$

where $a_n^{tflu}(\eta)$ is a $n^{th}$ order theoretical Fourier coefficient of the topography after creep for a time $t_{flu}$, $a_n^0$ is a $n^{th}$ order coefficient of the topography measured on the impressed pattern after creep, and $\tau_n$ is a relaxation coefficient of the layer, associated with the viscosity $\eta$ by the relationship $$\tau_n=3\eta(1/\gamma h_0^3)(L/2\pi n)^4,$$

in which $\gamma$ is a surface tension of the thin layer; $h_0$ is its average thickness, and L is the total length of the impressed pattern.

11. The method as claimed in claim 9, wherein a calculation of an $n^{th}$ order theoretical coefficient of the Fourier transform for a hypothetical viscosity $\eta$ is done by the following formula:

$$a_n^{tflu}(\eta)=a_n^0 \exp(-t_{flu}/\tau_n),$$

where $a_n^{tflu}(\eta)$ is a $n^{th}$ order theoretical Fourier coefficient of the topography after creep for a time $t_{flu}$, $a_n^0$ is a $n^{th}$ order coefficient of the topography measured on the impressed pattern after creep, and $\tau_n$ is a relaxation coefficient of the layer, associated with the viscosity $\eta$ by the relationship $$\tau_n=\tau_{relax}+3\eta(1/\gamma h_0^3)(L/2\pi n)^4,$$

in which $\gamma$ is a surface tension of the thin layer; $h_0$ is its average thickness, and L is the total length of the impressed pattern, and $\tau_{relax}$ is a characteristic relaxation time of elastic strains, the calculation being carried out for various hypothetical viscosities $\eta$ and various characteristic times $\tau_{relax}$, and an optimal pairing of a viscosity $\eta_{opt}$ and a characteristic time $\tau_{relax-opt}$ being selected in the optimal correlation search.

12. The method as claimed in claim 11, wherein a modulus of elasticity of the material in a thin layer is further calculated by the formula:

$$E=\eta_{opt}/\tau_{relax-opt}.$$

13. The method as claimed in claim 1, wherein the position of a creep front along a pattern whose period varies continuously is observed, and a value of the viscosity is deduced from this position.

14. The method as claimed in claim 1, wherein the same thin layer is used for a plurality of successive measurements at the same measurement temperature for successive times, or at different temperatures.

* * * * *